United States Patent [19]

Charlesworth et al.

[11] Patent Number: 5,132,066
[45] Date of Patent: Jul. 21, 1992

[54] METHOD OF FORMING A BIO-COMPATIBLE VASCULAR PROSTHESIS

[75] Inventors: David Charlesworth, Knutsford; Kerm S. Chian; Christopher J. Underwood, both of Manchester, all of England

[73] Assignee: Newtec V.P. Limited, Clwyd, Wales

[21] Appl. No.: 588,480

[22] Filed: Sep. 26, 1990

Related U.S. Application Data

[63] Continuation of Ser. No. 132,330, Dec. 14, 1987, abandoned.

[30] Foreign Application Priority Data

Apr. 9, 1987 [GB] United Kingdom ............... 8708476

[51] Int. Cl.$^5$ .............................................. D01F 6/00
[52] U.S. Cl. .................... 264/184; 264/209.2; 264/312
[58] Field of Search ............ 264/184, 201, 310, 209.2, 264/312

[56] References Cited

U.S. PATENT DOCUMENTS

| | | | |
|---|---|---|---|
| 3,339,000 | 8/1967 | Vance | 264/184 |
| 4,173,689 | 11/1979 | Lyman | 521/64 |
| 4,294,638 | 10/1981 | Rasmussen | 264/310 |
| 4,725,273 | 2/1988 | Kira | 623/1 |
| 4,834,746 | 5/1989 | Kira | 623/1 |

FOREIGN PATENT DOCUMENTS

| | | |
|---|---|---|
| 0129396 | 12/1984 | European Pat. Off. . |
| 0143638 | 6/1985 | European Pat. Off. . |
| 157178 | 10/1985 | European Pat. Off. . |
| 128501 | 5/1989 | European Pat. Off. . |
| 130401 | 5/1989 | European Pat. Off. . |
| 1504390 | 2/1970 | Fed. Rep. of Germany . |
| 8601095 | 2/1986 | PCT Int'l Appl. . |
| 454013 | 9/1936 | United Kingdom . |
| 708844 | 5/1954 | United Kingdom . |
| 859493 | 1/1961 | United Kingdom . |
| 1232153 | 5/1971 | United Kingdom . |
| 2102821 | 2/1983 | United Kingdom . |
| 2130521 | 6/1984 | United Kingdom . |

*Primary Examiner*—Hubert C. Lorin
*Attorney, Agent, or Firm*—Oblon, Spivak, McClelland, Maier & Neustadt

[57] ABSTRACT

A method of forming a bio-compatible vascular prosthesis comprising making a polymer material by coagulation in which the polymer, dissolved in an organic solvent, is formed into the material in a coagulant, the method being carried out at such low temperature as not substantially to degrade the polymer.

20 Claims, 5 Drawing Sheets

METHOD OF FORMING A BIO-COMPATIBLE VASCULAR PROSTHESIS

This application is a continuation of application Ser. No. 07/132,330, filed on 12/14/87, now abandoned.

BACKGROUND TO THE INVENTION

1. Field of the Invention

This invention relates to methods of and on apparatus for making polymer material and to novel polymer material made by such methods and apparatus.

2. Discussion of the Background

The novel polymer material is useful as a synthetic arterial prosthesis, and the methods and apparatus are adapted to produce such tubular material.

In GB-2 130 521 B there is described the production of a synthetic arterial prosthesis comprising a cellular polyurethane tube preformed by coagulation casting on to a former. A water soluble coating having a smooth surface is separately applied to another former and a polyurethane film is solvent cast on to the coating. The preformed tube is subsequently shrunk on to the film and the former is removed by dissolving the coating in water.

The resultant materials are said to be compliant to pulsatile flow, the inner film being smooth to within a tolerance of 10 microns for minimizing frictional energy losses at the wall of the tube and inhibiting pooling of procoagulents and the adhesion of platelets, which would ultimately give rise to thrombosis. The purpose of the water soluble coating was to produce such a smooth inner surface.

It is now found that it is unnecessary to use such a coating for this purpose.

The shrinking and bonding of the tube on to the film was, in GB-2 130 521 B, effected by heat—the assembly as subjected to a temperature of 100° C. for an hour. The bonded assembly was then suspended in a circulating bath of water typically at 80° C. for half an hour to dissolve the polyvinyl-alcohol release agent.

It is now found that at such high temperatures, extended treatments can degrade the polymer material to the extent that there is a risk of failure in use.

SUMMARY OF THE INVENTION

The present invention provides new methods of and an apparatus for making polymer materials which do not suffer from this disadvantage.

The invention comprises a method for making a polymer material by coagulation in which the polymer, dissolved in an organic solvent, is formed into the material in a coagulant, the method being carried out at such low temperatures as not substantially to degrade the polymer.

The method is preferably carried out at temperatures below or not substantially above 40° C., or blood temperature, if the polymer is bio-compatible and formed as a prosthesis, such as a vascular or arterial prosthesis.

The solution may contain a filler which is soluble in the coagulant, which may be water, so that the filler can be a water soluble substance such as sodium hydrogen carbonate. The filler may be ground to an average particle size of 60 microns and be present in an amount between 10 and 60 per cent by weight.

The solution may contain a surfactant which may be present in an amount between 1 and 10 per cent by weight.

The polymer may comprise polyurethane and may be a linear segmented poly(ether)urethane with an average molecular weight in the region 20,000 to 60,000 grams per mole.

The solvent may comprise an aprotic solvent such as N,N-dimethylacetamide or N,N-dimethylformamide. The concentration of polymer may be between 10 and 30 grams/decilitres.

The polymer solution may be injected to the forming process from a piston-in-cylinder arrangement in which the piston and cylinder are in relative rotation to impose a shearing force on the solution and thus effectively decrease its viscosity.

The polymer solution may be cast in tubular form on to a mandrel. The mandrel may have a smooth surface on to which the polymer solution is cast directly. The mandrel may be arranged to be horizontal in the coagulant and rotated about a horizontal axis so as to maintain the concentricity of the tubular form of the cast polymer solution during coagulation. An extrusion head through which the mandrel extends may rotate with the mandrel.

The coagulant may be maintained at a constant temperature throughout the coagulation process—for example, 40° C.—which may be continued for 1 to 2 hours. The coagulant may be circulated during the coagulation.

The invention also comprises an apparatus for making a polymer material tube by coagulation comprising a rotatable mandrel arranged horizontally in a coagulant bath and an extrusion head through which the mandrel extends, the head being adapted for rotation with the mandrel.

The invention also comprises an apparatus for injecting a viscous polymer into a material forming operation comprising a piston-in-cylinder arrangement in which the piston and cylinder are relatively rotatable to apply a shear force to the viscous polymer thereby reducing its effective viscosity.

The invention, in a broader aspect, comprises an apparatus for making a polymer material by coagulation at such low temperatures as not to substantially degrade the polymer, comprising means for controlling the viscosity of a polymer solution from which the material is formed by coagulation by controlling shear forces thereon.

The solution may be injected in a forming process by injection means applying a shear force to reduce the effective viscosity thereof. The injection means may comprise a piston-in-cylinder arrangement of which the piston and cylinder are relatively rotatable to reduce the effective viscosity of the solution. Forming means may, in contrast, apply no or substantially no shear force to the solution in forming the material.

Polymer material suitable for use in tubular form as an arterial prosthesis may be produced comprising a microporous, bio-compatible polymer having elastic extensibility and compressibility similar to those of natural artery material. The invention also comprises an arterial prosthesis of such material having a wall thickness of one millimeter and an internal diameter of 4 mm.

BRIEF DESCRIPTION OF THE DRAWINGS

Embodiments of the apparatus and methods for making a polymer material, all according to the invention, will now be described with reference to the accompanying drawings, in which.

DESCRIPTION OF THE PREFERRED EMBODIMENT

The drawings illustrate an apparatus for making a synthetic polymer tube which is suitable as a vascular or arterial prosthesis. The tube is made by coagulation.

The polymer, a medical grade linear segmented poly(ether)urethane with a number average molecular weight in the range 20,000 to 60,000 grams per mole is dissolved in an aprotic organic solvent, for example, N,N-dimethylacetamide or N,N-dimethylformamide to a concentration of between 10 and 30 grams/deciliter at a temperature less than 30° C. A water soluble filler is then added, for example ground particles of sodium hydrogen carbonate with an average diameter of 60 microns, to a concentration between 10% and 60% by weight, followed by a surfactant, for example sodium dodecylsulphate at a concentration between 1% and 10% by weight.

Figure 1:
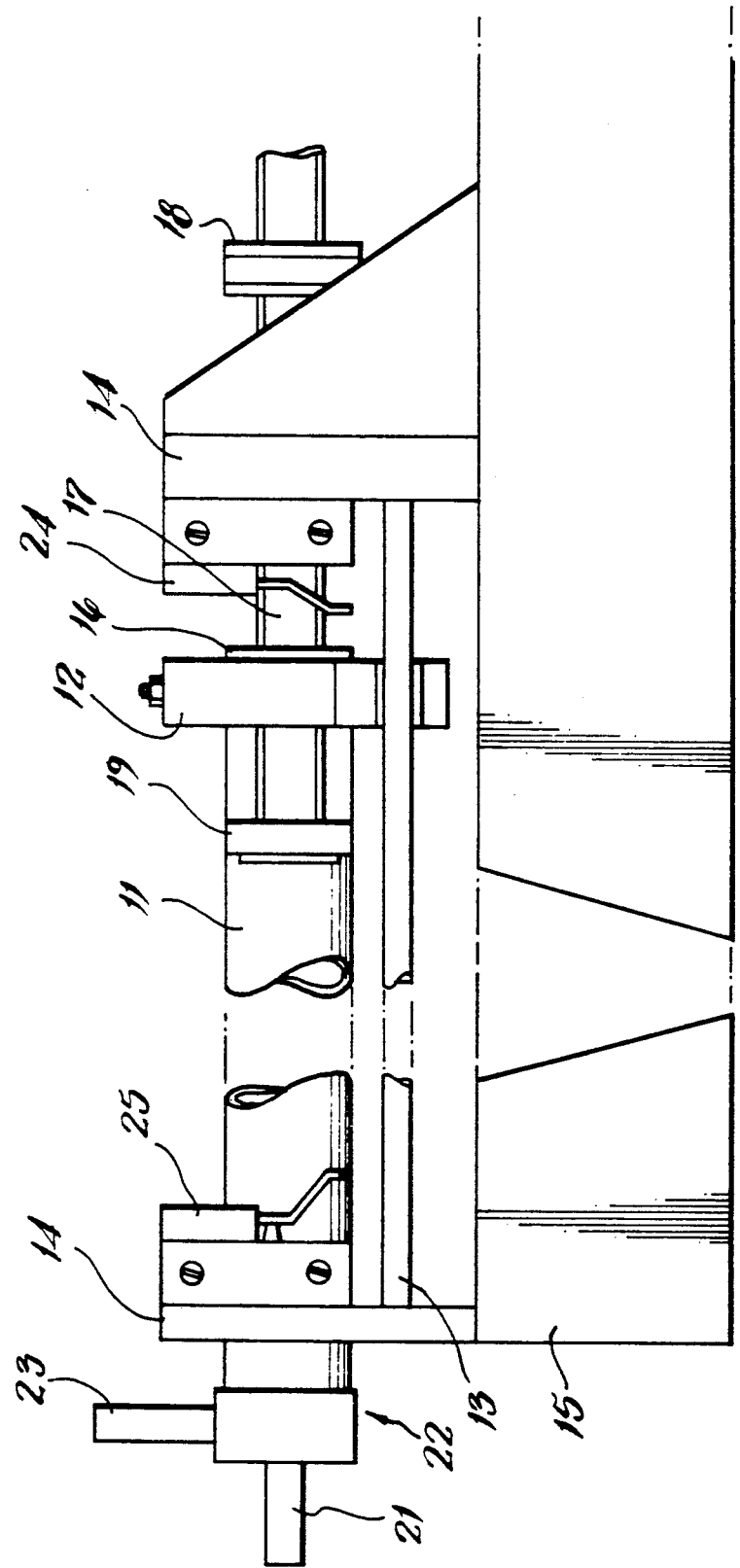
FIG. 1 is a side elevation of an injection unit.
Figure 2:
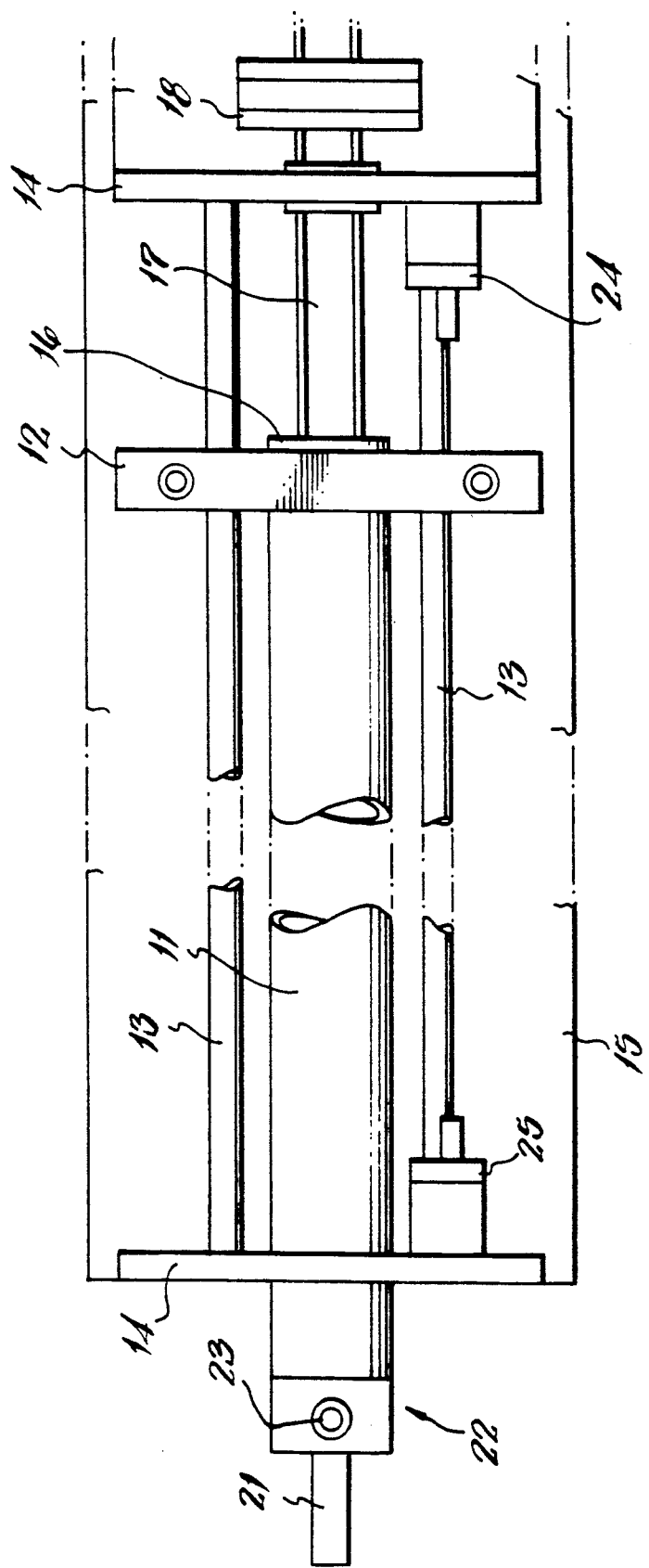
FIG. 2 is a plan view of the injection unit illustrated in FIG. 1.

The solution is loaded into a piston-in-cylinder syringe arrangement illustrated in FIGS. 1 and 2. The cylinder 11 is adapted to move axially and is attached to a yoke 12 slidable on guide rods 13 extending between end pieces 14 of a base 15. The yoke 12 has a nut 16 engaging a lead screw 17 which extends through a bearing in the right hand end piece 14, as seen in the drawings, and which is rotated by a motor (not shown) through a coupling 18. A piston 19 is on the other, left hand, end of the lead screw 17 and thus rotates with it. The cylinder 11 does not, of course, rotate since it is constrained by the guide rods 13.

An outlet port 21 is provided at the nozzle end 22 of the cylinder 11 remote from the yoke 12, as well as a closable air vent 23.

Microswitches 24, 25 are provided on the end pieces 14 which are actuated by the yoke 12 indicating it is at one or the other end of its range of travel.

The full cylinder 11 starts from an extended position left of that illustrated in FIGS. 1 and 2 and moves to the right under the action of the lead screw 17 pumping the solution out of the nozzle.

Figure 3:
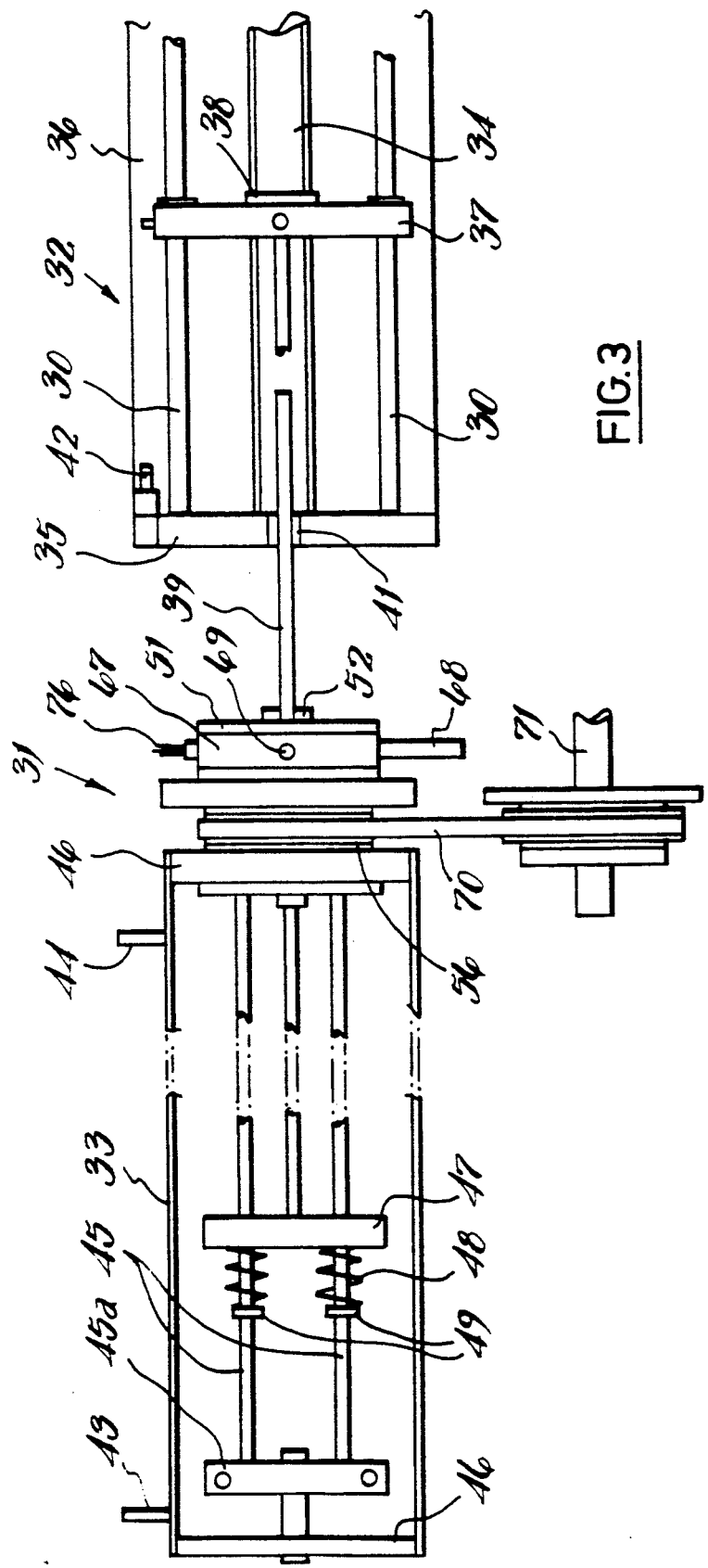
FIG. 3 is a plan view of an extrusion arrangement.

The outlet port 21 is connected by a medical grade thick walled silicone rubber tubing to the extrusion arrangement illustrated in FIG. 3.

The extrusion arrangement comprises generally an extrusion head 31, illustrated in more greater detail in FIGS. 4 to 7, a mandrel drive unit 32 and a coagulation bath 33.

The mandrel drive unit 32 has a lead screw 34 supported between end pieces 35, of which only one is shown, of a base 36 and rotated by an electric motor not shown in this Figure. There are guide rods 30 also extending between the end pieces 35. A yoke 37 has a nut 38 engaging the lead screw 34 and runs on the guide rods 36. The yoke 37 is driven from the right, as seen in FIG. 3, to the left and pushes a mandrel 39 through a ptfe bearing 41 in the left hand end piece 35.

A microswitch 42 is actuated by the yoke 37 indicating that it has reached the left hand extremity of its travel.

The mandrel 39 is thus forwarded through the extrusion head 31 and into the coagulation bath 33.

In the bath 33, which is supplied with circulating, temperature controlled water through inlet and outlet ports 43, 44, are further guide rods 45 extending along the bath. A yoke 47 is slidable on these guide rods 45 from right to left as seen in the drawing against a resistive force from springs 48 and clips 49 on the guide rods 45. The yoke 47 is pushed along the guide rods 45 by the advancing mandrel 39. The guide rods 45 revolve about the mandrel 39 being carried in a bearing 45a at the left hand end wall 46 and in the rotary extrusion head 31.

Figure 4:
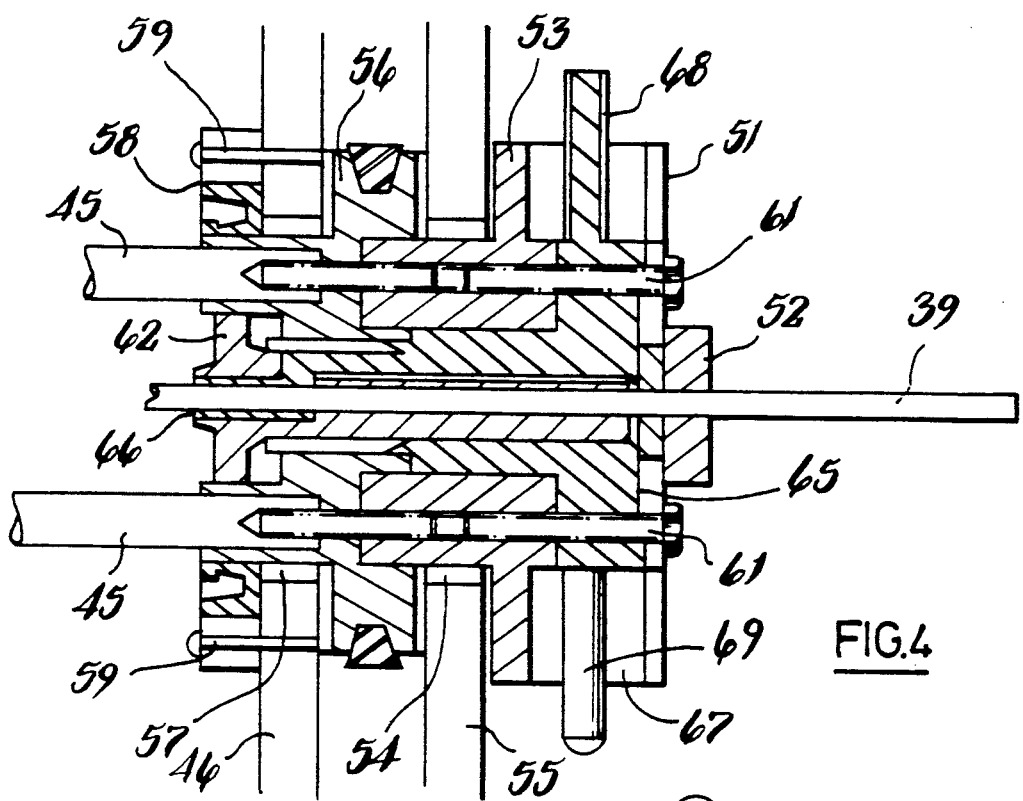
FIG. 4 is an axial cross-section of an extrusion head of the arrangement illustrated in FIG. 3.

FIG. 4 illustrates the extrusion head 31 in further detail. It comprises a body made up from an outer plate 51 with a central ptfe locating port 52 connected to a central member 53 carried in a ptfe bearing 54 in a frame member 55 and a pulley member 56 supported in a ptfe bearing 57 in the end wall 46 of the coagulating bath 33. The bearing 57 is held in position in the end wall 46 seal arrangement 58 secured by screws 59.

The plate 51, central member 53 and pulley member 56 are held together by bolts 61, which also secure the guide rods 45, which thereby revolve about the mandrel 39 as noted above.

Figure 6:
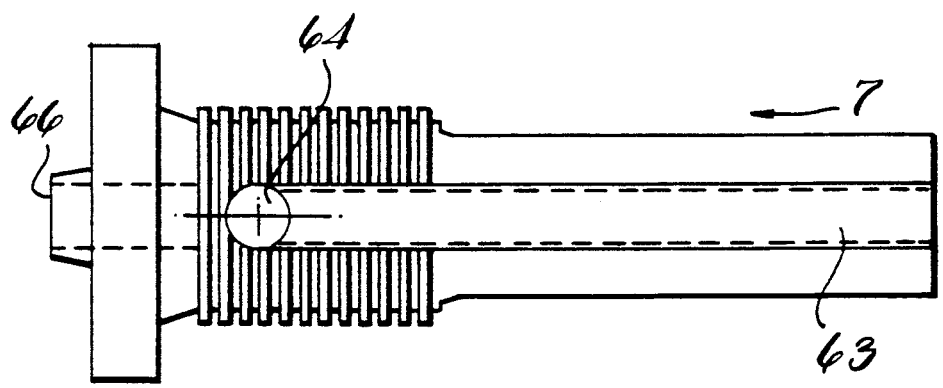
FIG. 6 is a side view of a die used in the extrusion head illustrated in FIG. 3.
Figure 7:
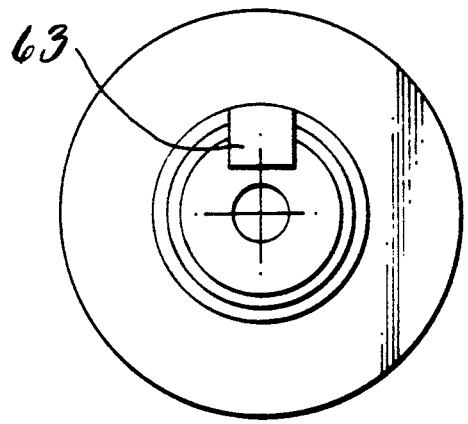
FIG. 7 is an end view in the direction of arrow 7 on FIG. 6.

A die 62 shown in larger scale in FIGS. 6 and 7 comprises a ptfe member which extends through the extrusion head 31 from the outer plate 51 into the coagulating bath 33 and comprises a channel 63 and a bore 64 through which the solution passes from a solution chamber 65 in the extrusion head to the die orifice 66. The ptfe locating port 52 and the die 62 have precision bores of the same diameter as the mandrel 39 which are self-sealing against leakage when the mandrel is in place and which centralize the mandrel 39 in the die orifice 66.

Figure 5:
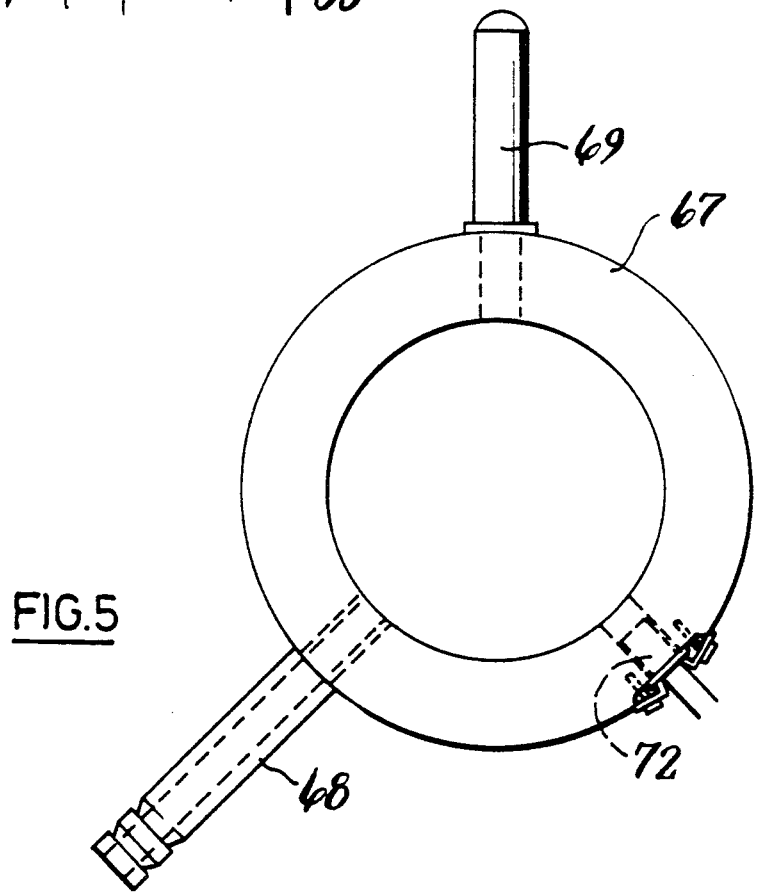
FIG. 5 is an end view of an inlet manifold of the extrusion head illustrated in FIG. 3.

The solution chamber 65 is bounded by the outer plate 51, the central member 53 and a ptfe inlet manifold 67, illustrated further in FIG. 5. The manifold 67 comprises an annular member having an injection port 68 which is connected to the syringe arrangement of FIGS. 1 and 2 by the medical grade thick walled silicone rubber tubing mentioned above. The manifold 67 is prevented from rotating with the rest of the extrusion head by a movement restrictor 69 engaging the frame member 55. The head 31 is rotated by a v-belt 70 engaging the pulley member 56 and driven from a motor driven shaft 71.

The manifold 67 houses a pressure transducer 72 which is used in the control of the process.

The mandrel 39 rotates with the extrusion head 31 because it is securely gripped along the length of the bore of the die 62 and the locating port 52 as well as by the yoke 47 in the coagulation bath 33.

The purpose of the rotation is to maintain concentricity of the solution extruded on to the mandrel 39 during coagulation. The reason for rotating the die 62 as well as the mandrel 39 is to eliminate shear forces on the solution as it is being cast on to the mandrel 39.

Figure 8:
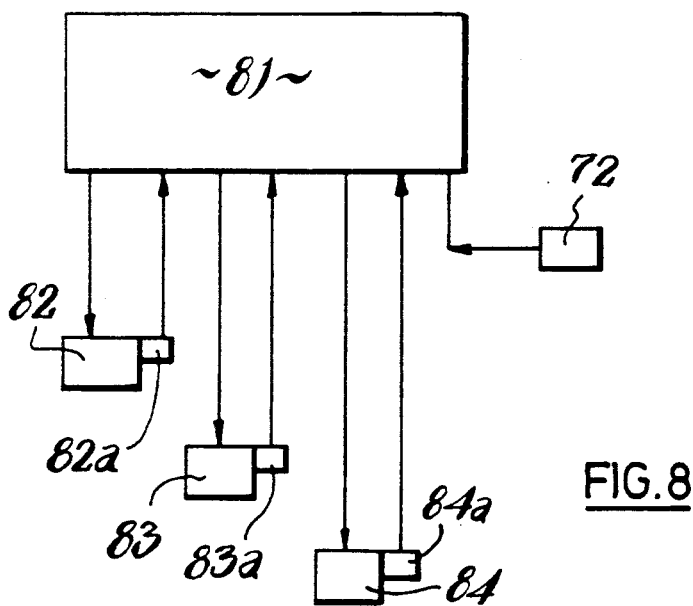
FIG. 8 is a diagrammatic illustration of a control system.

FIG. 8 shows a control arrangement in which a microprocessor based control unit 81 controls the motor 82 that drives the injection unit of FIGS. 1 and 2, the motor 83 that drives the mandrel drive unit 32 and the motor 84 that rotates the extrusion head 31. A four channel feed back system uses opto-electronic transducers 82a, 83a and 84a on the shafts of the motors 82, 83 and 84 as well as the pressure transducer 72. The motors are d.c. motors which are regulated by pulse width modulation of the supply voltage.

In operation, after the injection unit has been filled with air vented through vent 23, the control unit 82 is powered up and set to manual while the mandrel 39 is positioned in the locating port 52 of the extrusion head 31. The injection unit is then turned on and polymer solution allowed to flow slowly into the extrusion head 31 and purge the solution chamber and flow channels of air. The mandrel 39 is then moved in to seal the die orifice and the bath 33 is filled with circulating water, which is usually, but not necessarily, the coagulant maintained at 40° C. The control unit 81 is then turned to automatic. In rapid (i.e. 3 second delay) sequence the injection unit motor 82, then the mandrel drive unit motor 83 and finally the extrusion head rotation motor 84 are gradually (over about 5 seconds) powered up to predetermined levels.

When the mandrel has been fully coated, the polymer solution is allowed to coagulate for one or two hours in the bath 33, rotation of the mandrel 39 and circulation of the temperature controlled coagulant being maintained throughout this period.

The coagulation bath 33 is then drained and the mandrel removed. The arterial prosthesis, now fully formed, is removed from the mandrel, rinsed in distilled water and placed in dilute hydrochloric acid for half an hour to remove any last traces of filler. The prosthesis is finally rinsed thoroughly in deionized water and stored prior to sterilization.

The coagulation bath 33 is of the order of 1 meter in length, and the mandrel 39 will be of comparable length so as to be able to extend substantially through the bath.

The mandrel used is a polished steel rod of circular cross-section which is 4 mm in diameter. The die 62 is such that the thickness of the solution extruded on to the mandrel is 1 mm.

The result is a length of synthetic arterial prosthesis which is bio-compatible and which closely approximates a natural artery in its mechanical properties as regards strength, elastic extensibility and compressibility.

The methods and apparatus described are of course not limited to the production of tubular prostheses—more complicated shapes could be produced by different forming techniques which yet still utilize the principles of the invention.

We claim:

1. A method of forming a bio-compatible vascular prosthesis which comprises the steps of:
    (a) forming a solution of a coagulatable, bio-compatible polymer in an organic solvent;
    (b) extruding the solution through an extrusion head on to a mandrel having an axis being fed axially through the extrusion head together with the extruding solution, the extrusion being directed into a coagulant liquid which coagulates the polymer into a hollow polymer extrusion on the mandrel;
    (c) simultaneously rotating the mandrel and the extrusion head about the axis of the mandrel during the extrusion; and
    (d) removing the mandrel to form a vascular prosthesis which closely approximates a natural artery in its elastic extensibility and compressibility.

2. A method according to claim 1, in which the method is carried out at temperature not exceeding about 40° C.

3. A method according to claim 1, in which the solution further comprises a filler soluble in the coagulant.

4. A method according to claim 3 in which the filler is sodium hydrogen carbonate.

5. A method according to claim 3, in which the filler is ground to an average particle size of 60 microns.

6. A method according to claim 3, in which the filler comprises between 10 and 60 percent of the weight of said solution.

7. A method according to claim 1, in which the solution comprises surfactant which comprises between 1 and 10 percent of the weight of said solution.

8. A method according to claim 1, in which the polymer comprises polyurethane.

9. A method according to claim 8, in which the polyurethane is a linear segmented poly(ether)urethane with a number average molecular weight in the region 20,000 to 60,000.

10. A method according to claim 1, in which the solvent is aprotic.

11. A method according to claim 1, in which the solvent comprises N,N-Dimethylacetamide.

12. A method according to claim 10, in which the solvent comprises N,N-Dimethylformamide.

13. A method according to claim 1, in which the said solution is injected from a piston in cylinder arrangement of which the piston and cylinder are in relative rotation to impose a shearing force on the said solution and thus in effect decrease its viscosity.

14. A method according to claim 1, in which the mandrel has a smooth surface on to which the polymer solution is cast directly.

15. A method according to claim 1, in which the mandrel is arranged to be horizontal in the coagulant and is rotated about a horizontal axis so as to maintain the concentricity of the tubular form of the cast polymer solution during coagulation.

16. A method according to claim 15, in which an extrusion head through which the mandrel extends rotates with the mandrel.

17. A method according to claim 1, in which the coagulant comprises water.

18. A method according to claim 17, in which the coagulant is maintained at a constant temperature throughout the coagulation process.

19. A method according to claim 1, in which the coagulation is maintained for 1 to 2 hours.

20. A method according to claim 1, in which the coagulant is circulated during coagulation.

* * * * *